United States Patent [19]

Williams

[11] 3,952,733
[45] Apr. 27, 1976

[54] ARM SUPPORT
[76] Inventor: Ester B. Williams, 4807 Gilray Drive, Baltimore, Md. 21214
[22] Filed: Apr. 23, 1975
[21] Appl. No.: 570,739

[52] U.S. Cl. .................................. 128/94; 128/83
[51] Int. Cl.² ................................. A61F 5/40
[58] Field of Search ................. 128/94, 88, 87, 86, 128/85, 84, 83, 82

[56] References Cited
UNITED STATES PATENTS

| 890,842 | 6/1908 | Cheatham | 128/94 |
| 1,011,146 | 12/1911 | Baxter | 128/94 |
| 1,043,648 | 11/1912 | Weaver | 128/94 |
| 1,257,297 | 2/1918 | Brown | 128/94 |
| 1,921,987 | 8/1933 | Ettinger | 128/88 |
| 1,961,118 | 5/1934 | Ettinger | 128/88 |
| 2,010,328 | 8/1935 | Siebrandt | 128/88 |
| 2,191,283 | 2/1940 | Longfellow | 128/88 |

Primary Examiner—John D. Yasko
Attorney, Agent, or Firm—J. Wesley Everett

[57] ABSTRACT

The improved arm support is supported from the waist of the patient and comprises a short length of substantially solid material for engaging the patient's waist and is held in place about the waist by a flexible belt-like member. Secured to the waist support is an adjustable bracket extending obliquely outwardly and upwardly from the upper edge of the waist engaging member to an arm resting element extending substantially perpendicular to the bracket.

1 Claim, 7 Drawing Figures

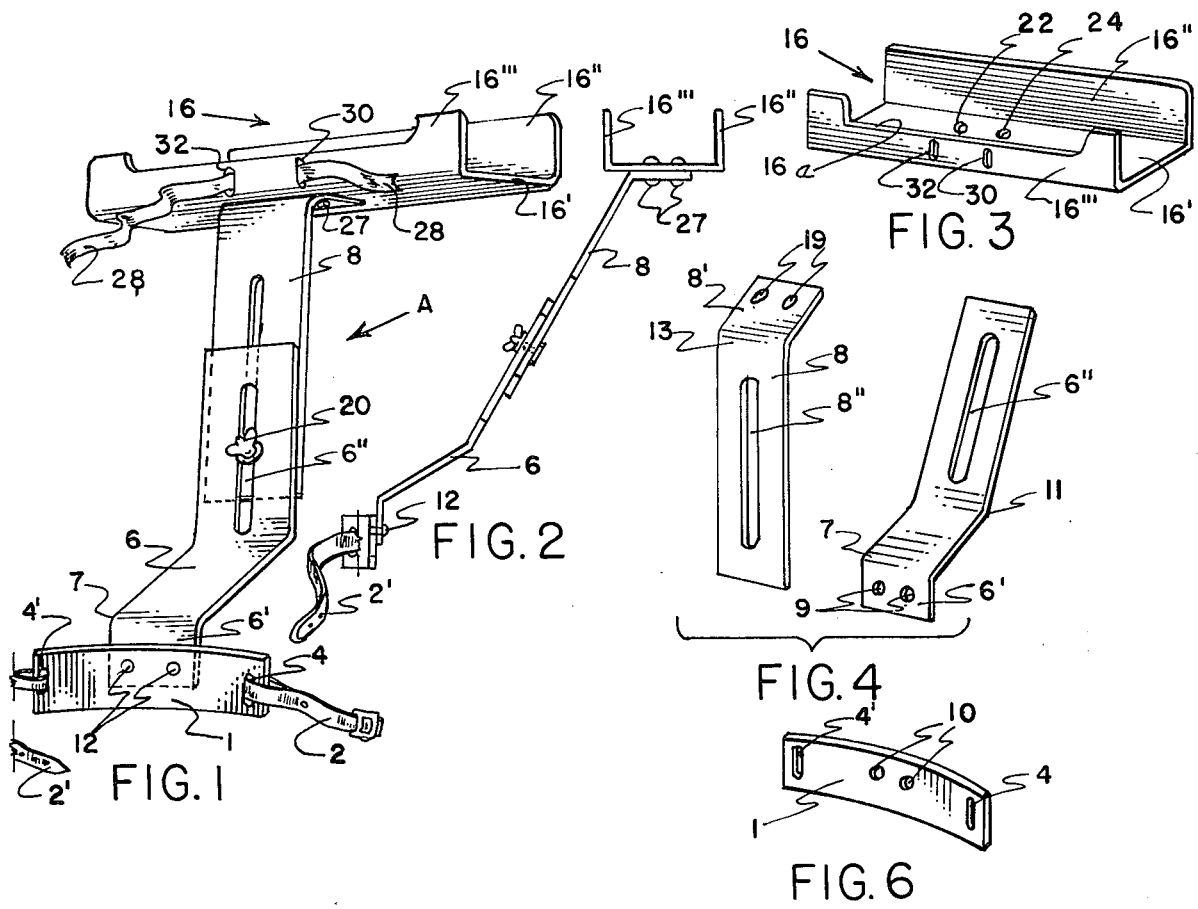
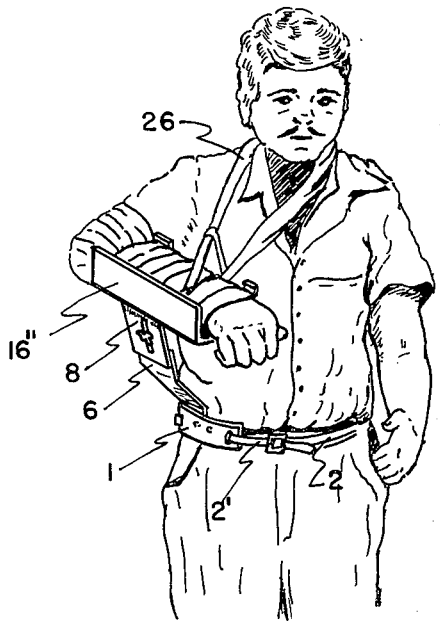

ARM SUPPORT

The present invention relates to an improved arm support.

One object of the invention is to provide an arm support in which the fulcrum of the support is at the patient's waist.

Another object of the invention is to provide an arm rest that is easily adjusted to a height in relation to the patient's body.

A further object of the invention is to provide an arm rest that will serve individuals of different sizes.

While several objects of the invention have been noted, other objects, uses and advantages will become apparent as the nature of the invention is more fully disclosed from the following detailed description with reference to the accompanying drawings in which:

FIG. 1 is a view in perspective of the assembled arm support.

FIG. 2 is a side view of the same.

FIG. 3 is a perspective view of the arm supporting element.

FIG. 4 is a perspective view of two bracket elements for supporting the arm supporting element.

FIG. 5 is a view in elevation showing means for holding the adjustable members in position.

FIG. 6 is a perspective view of the waist contact member.

FIG. 7 is a front view in elevation of a patient wearing the arm support, showing the manner in which the support is attached to the patient.

When referring to the drawings, like reference characters are used to designate like and similar parts throughout the several views.

FIGS. 1 and 2 show the arm support assembled ready to be worn by a patient.

The arm support A is provided with a waist engaging member 1 which is adapted to fit the curvature of the side of the patient's body. Extending about the remainder of the waist is a flexible belt 2 and 2' secured into suitable openings 4 and 4' in each end of the waist member 1.

Secured substantially centrally of the waist member 1 is a two part adjustable bracket formed by the two members 6 and 8 and slideable relative to each other. One end 6' of the part 6 is angled outwardly at 7 and is secured to the waist member 1 by rivets 12, extending through the hole 9 on the bracket member and through the holes 10 on the waist member 1. The upper portion 6' of the bracket 6 is angled obliquely inwardly at 11 at a smaller angle than the angle 7 and is provided with an elongated slot 6'', the purpose of which will be referred to later.

The other member 8 of the bracket is also provided with an outwardly oblique angled portion 8' as shown at 13 and is adapted to extend beneath the arm rest member 16. The angled portion 8' is secured to the arm rest member 16 by the rivets 27 extending through the holes 22 and 24 in the member 16 and the holes 19 in the bracket member 8. The member 8 is also provided with a slot 8''. The two members 6 and 8 are held in adjustable relationship by the thumb screw 20 and the bolt 21. A sling 26 is normally used to support the arm in the rest element 16 at a predetermined distance from the patient's body.

The arm rest element 16 may also be supported by a tie element 28 which may extend through the apertures 30 and 32 and adapted to be secured to or about the upper portion of the patient's body which leaves the patient's arm free within the arm rest member 16.

The arm support is preferably made from "plexiglass", a trade name for a very durable plastic material; however any suitable material may be used.

The improved arm support has the advantage of supporting most of the weight about the patient's waist. It also has the advantage of supporting the arm outwardly from the body at the proper distance and at the proper angle.

The side 16''' is cut down as shown at 16a in order not to interfere with the sling 26 or similar tie members for holding the arm in the resting element.

While the various elements are shown connected to each other by rivets, they may be fastened to each other by gluing, welding, or any other suitable means or method or they may be stamped or molded from any suitable material.

While the invention is shown in a specific form it is not intended as a limitation as the scope of the invention is best defined in the appended claims.

I claim:

1. An arm support comprising a short, flat, concave, rigid body-engaging member having an opening in each end thereof for attaching a belt thereto for encircling the waist of the wearer, a bracket section having one end thereof adapted to be fixed to the said body-engaging member along one of its flat sides, said bracket section being angled outwardly at an obtuse angle immediately above the body-engaging member, a second obtuse angle formed in the opposite direction in the said bracket section outwardly from the first obtuse angle, a second bracket section of substantially the same width and length as the first bracket section, the outer end of which is formed outwardly at an angle perpendicular to the rigid, flat, body-engaging member, an arm supporting member having a bottom and two side walls, the outer side wall being higher than the inner side wall, said bottom being fixed to the angled portion of the second section of the bracket, the second section of the bracket having a central slot therein for adjusting the same relative to the first bracket section, and a thumb screw adapted to clamp the two bracket sections in adjusted fixed position, the shorter side wall of the arm support having slots therein and means extending through said slots and adapted to extend about a part of the body of the wearer for limiting the outward movement of the arm supporting member.

* * * * *